United States Patent [19]

Sweeney

[11] Patent Number: 4,527,004

[45] Date of Patent: Jul. 2, 1985

[54] PURIFICATION OF OLEFINS BY BORON TRIFLUORIDE-ALCOHOL TREATMENT

[75] Inventor: William A. Sweeney, Larkspur, Calif.

[73] Assignee: Chevron Research Company, San Francisco, Calif.

[21] Appl. No.: 382,904

[22] Filed: May 28, 1982

[51] Int. Cl.³ .............................................. C07C 7/10
[52] U.S. Cl. .................................... 585/851; 585/833; 208/292
[58] Field of Search ................. 585/833, 851; 208/292

[56] References Cited

U.S. PATENT DOCUMENTS

| | | | |
|---|---|---|---|
| 2,065,540 | 12/1936 | Schneider | 585/833 |
| 2,993,933 | 4/1961 | Brown | 585/833 |
| 3,023,255 | 2/1962 | Lang et al. | 585/851 |
| 3,367,987 | 2/1968 | Walsh | 585/851 |

Primary Examiner—Delbert E. Gantz
Assistant Examiner—Cynthia A. Prezlock
Attorney, Agent, or Firm—D. A. Newell; T. G. De Jonghe; C. J. Caroli

[57] ABSTRACT

A process for purifying predominantly straight chain olefins having from 5 to 50 carbon atoms which comprises contacting the olefins with a liquid solution of boron trifluoride in an alcohol or mixture of alcohols.

9 Claims, No Drawings

PURIFICATION OF OLEFINS BY BORON TRIFLUORIDE-ALCOHOL TREATMENT

BACKGROUND OF THE INVENTION

The present invention relates to a process for the purification of predominantly straight chain olefins. It is particularly useful for purifying alpha-olefins derived from the cracking of petroleum hydrocarbons. More specifically, the process of the invention involves treating the olefins with a liquid boron trifluoride-alcohol solution.

Olefins formed by wax cracking of petroleum hydrocarbons contain certain impurities which lead to color formation and limit the reactivity of these olefins in many reactions, such as alkylation, oxo reactions, sulfonation, and polymerization, including oligomerization to form synlube materials and copolymerization with ethylene. These impurities may include conjugated and unconjugated dienes as well as other olefins, aromatics and paraffins. In the past, various treatments have been proposed to purify cracked wax olefins, including treatment with sulfuric acid, and the like. See, for example, U.S. Pat. No. 3,094,570. However, these treatments are usually only partially effective or are impractical. Often, yield losses are too high, the reagent is too expensive, or the alpha-olefin is isomerized.

SUMMARY OF THE INVENTION

It has now been found that predominantly straight chain olefins having from 5 to 50 carbon atoms can be purified by contacting the olefin with a liquid solution of boron trifluoride in a low molecular weight alcohol or mixture of alcohols.

Among other factors, the present invention is based on the discovery that predominantly straight chain olefins can be purified by treatment with certain boron trifluoride-alcohol solutions under reaction conditions which minimize the degree of olefin reactions normally catalyzed by $BF_3$, such as isomerization, while thereby recovering a purified olefin product which is essentially free of deleterious impurities.

It is known that boron trifluoride-alcohol complexes catalyze olefin reactions such as isomerization, polymerization, alkylation, and the like. For example, U.S. Pat. Nos. 4,209,654 and 4,227,027 describe alkylation and polymerization reactions using $BF_3$.poly-ol complexes as catalyst. The present invention, on the other hand, uses $BF_3$.alcohol solutions to purify olefins while avoiding these well known reactions.

Predominantly straight chain olefinic hydrocarbons in the $C_5$–$C_{50}$ range containing varying degrees of impurities may be treated according to the process of the invention. Accordingly, the present process may be utilized to purify $C_5$–$C_{25}$ alpha-olefins obtained from the Fischer-Tropsch process, $C_5$–$C_{25}$ n-olefins obtained by dehydrogenating n-paraffins, or the $C_{10}$–$C_{50}$ olefins obtained by oligomerizing straight chain olefins in the $C_5$–$C_{25}$ range. A preferred feed for the process is a fraction of normal alpha-olefins in the $C_5$–$C_{25}$ range obtained by the cracking of petroleum waxes. By treating the olefins under conditions described in this invention, substantially all of the impurities which retard or suppress further reaction of the olefins are removed while isomerization is minimized. Thus after treatment, a polymerization reaction, for example, may be successfully carried out at a suitable rate on the treated olefins.

The process of the invention may be further described as follows. A liquid solution of boron trifluoride in an alcohol or mixture of alcohols is added to the liquid predominantly straight chain olefins. The two liquids are intimately admixed and then separated into two liquid layers. The olefin layer is recovered by conventional techniques to give an olefin product wherein a maximum amount of impurities has been removed. It is preferred that the $BF_3$.alcohol solution be relatively low in viscosity and high in density so that the separation will be fast and the alcohol layer easy to remove.

The alcohols utilized in this process are the normally liquid low molecular weight mono and poly hydroxylic aliphatic compounds having from one to five carbon atoms. Mono-ols of six or more carbon atoms have been found to be unsatisfactory. Also unsuitable are high molecular weight poly-ols, which form viscous or solid $BF_3$ complexes, such as those described in U.S. Pat. Nos. 4,209,654 and 4,227,027. The mono-ols employed in the present process are preferably primary alcohols and typically include methanol, ethanol, butanol and 3-oxabutanol. Poly-ols such as ethylene glycol, propylene glycol, glycerol, and the like, are advantageous for the present process because of their high density and low hydrocarbon solubility. However, because their $BF_3$ complexes are very viscous, it is preferable to use the poly-ols in a mixture with a mono-ol. A mixture of methanol and ethylene glycol has been found to be a particularly effective combination. The relative amounts of the components in these mixtures of alcohols may vary over a wide range. Thus, for a two component system, the relative amounts of alcohols may range from about 4:1 to 1:4 on a weight basis.

The boron trifluoride-alcohol mixture contains from about 0.1 mole of boron trifluoride per mole of hydroxyl group up to saturation of the hydroxyl groups with boron trifluoride. In this context, saturation is taken to mean the maximum amount which readily dissolves at room temperature and atmospheric pressure. This is about one boron trifluoride molecule per hydroxyl group for the mono-ols but is less for poly-ols. Generally, excess or uncomplexed boron trifluoride will not be present in the system and it is preferred that the amount of boron trifluoride be about 70 to 98% of saturation.

The $BF_3$.alcohol complexes may be prepared in different ways. A prescribed weight of $BF_3$ can be bubbled into the alcohol or an excess of $BF_3$ can be bubbled through until it is no longer absorbed. Then, to achieve the desired $BF_3$ concentration, extra alcohol can be added before the treating step. An alternative method is to add $BF_3$ to a mixture of the alcohol and olefin to be treated. This must be done with a carefully measured amount of $BF_3$ and the mixture well stirred to avoid isomerization or polymerization of the olefin.

In general, the ratio of boron trifluoride-alcohol to olefin ranges between about 0.01:100 to 10:100, on a weight basis.

Typical treating conditions include intimate mixing for a period of time from about 1 second to 60 minutes, followed by settling out and removal of the $BF_3$ layer. Preferably, mixing time is from about 15 seconds to five minutes. Settling requires from about one to about 60 minutes. The $BF_3$ layer may be promptly withdrawn or allowed to sit for as long as a day or more. The temperature during contact is generally the ambient temperature. However, moderately higher or lower temperatures may be used and suitable temperatures include the range from about −20° C. to 80° C. Additionally, the water content should be kept to a minimum as best results are obtained when the system is substantially anhydrous.

The olefin may be treated one or more times with the $BF_3$ solution. After treatment the olefin may be used directly in such reactions as $BF_3$-catalyzed oligomerization or it may be cleaned of traces of residual $BF_3$ or alcohol using established techniques.

The separated $BF_3$.alcohol layer containing the impurities can be neutralized to release the impurities removed from the olefin. The $BF_3$ may be recovered for recycle using known techniques.

The present process may be conducted batchwise or in a continuous operation.

Predominantly straight chain olefins treated according to this invention can be readily polymerized at a rate comparable to that for noncracked-wax olefins, such as ethylene oligomers. It can be seen that by means of the treating process shown in this invention, olefins containing a relatively high level of impurities may be treated to render them readily usable to form olefin oligomers as well as intermediates for detergents, alcohols, plasticizers, and the like, useful to the chemical industry.

A convenient test for determining olefin quality consists of shaking 5 ml of the olefin with one drop of concentrated sulfuric acid. The amount of color and sludge which may form correlates with color formation and reactivity of the olefin in a variety of derivative-forming reactions. A high purity alpha olefin derived from ethylene gives almost no color and no sludge in this test. An untreated cracked wax olefin turns black and forms considerable sludge. Olefins treated by the present process show a marked improvement in this test. Generally, no sludge is formed and the color ranges from straw yellow to deep burgundy.

The following examples are provided to illustrate the invention in accordance with the principles of the invention but are not to be construed as limiting the invention in any way except as indicated by the appended claims.

EXAMPLES

Examples 1 to 4

Gaseous $BF_3$ at atmospheric pressure was bubbled into 32.04 g of dry methanol until the methanol was saturated with $BF_3$. The weight gain was 68.69 g which equals 1.01 moles of $BF_3$ per mole of methanol. This $BF_3$ solution was used for olefin treating experiments.

Similar solutions, as listed in Table 1, were made with the other monohydric alcohols, n-butanol, n-hexanol and n-decanol. In each case about 1 mole of $BF_3$ was absorbed per mole of alcohol.

Examples 5 and 6

Solutions were made as in Example 1 with the polyhydric alcohols, ethylene glycol and glycerine. See Table 1. These solutions were difficult to prepare as they became very viscous. With ethylene glycol, a solid gradually forms at room temperature. The amount of $BF_3$ absorbed was close to one mole per mole in each case, that is, one mole of $BF_3$ for the two hydroxyls in ethylene glycol and one mole for the three hydroxyls in glycerine.

Examples 7 to 11

Solutions of $BF_3$ were made as in Example 1 employing the mixed alcohols shown in Table 2. In each case no difficulty was experienced in preparing the solutions. Colorless, fluid solutions were obtained. The tendency of the poly-ols to form very viscous or solid mixtures was prevented by the presence of the mono-ol, methanol.

TABLE I

Saturated $BF_3$.Alcohol Solutions

| Example | Alcohol | $BF_3$ Amount % | Mol/Mol Alcohol | Appearance | Density g/ml |
|---|---|---|---|---|---|
| 1. | Methanol | 68 | 1.01 | Clear Fluid | 1.41 |
| 2. | n-Butanol | 45 | 0.89 | Clear Fluid | 1.13 |
| 3. | n-Hexanol | 39 | 0.98 | Sl. Yellow Fluid | — |
| 4. | n-Decanol | 25 | 0.77 | Sl. Yellow Fluid | — |
| 5. | Ethylene Glycol | 55 | 1.14 | V. Viscous; Solidifies on Standing | 1.55 |
| 6. | Glycerine | 37 | 0.8 | Too Viscous to Saturate at Room Temperature; with Heating, Got Dark Brown, Very Viscous Solution | — |

TABLE II $BF_3$ Mixed Alcohol Solutions

| Example | Alcohol Mixture | Weight Ratio Methanol/Poly-ol | $BF_3$ Amount % | Mol/Mol Alcohol |
|---|---|---|---|---|
| 7. | Methanol/Ethylene Glycol | 2.27 | 28 | 0.21 |
| 8. | " | 0.73 | 62 | 1.07 |
| 9. | " | 1.03 | 63 | 1.06 |
| 10. | " | 2.0 | 67 | 1.15 |
| 11. | Methanol/Glycerine | 1.0 | 60 | 1.05 |

Examples 12 to 20

Simple screening experiments were made by shaking for 30 seconds 10 ml of $C_{10}$ cracked wax alpha olefin in a stoppered graduate with 0.5 ml of various $BF_3$ solutions. After settling a short time, the appearance of the mixture was observed and, after standing at room temperature for one day, some of the upper layer was drawn off, filtered through anhydrous $K_2CO_3$ and an IR spectrum obtained.

In examples 13, 14, 17, 19 and 20, a very dark lower layer was observed, indicating that olefin impurities were being drawn into this layer.

Example 12 shows that BF$_3$ gas alone does not form a suitable fluid extract layer. Examples 15 and 16, employing the hexyl and decyl alcohol solutions, did not show a lower layer and therefore the solutions are not suitable for this process.

The fact that the 1-decene has partially reacted in several cases shows that conditions must be chosen to keep isomerization below a desired level. Strength of the reagent, time and temperature are variables that would be controlled. Although 20% isomerization may be acceptable for some uses, less than 5% isomerization may be required for others. Greater than 50% isomerization would generally not be acceptable. In these experiments, less than about 15% isomerization was considered acceptable.

TABLE III

| | | | | BF$_3$.Alcohol Olefin Treatment | | | | |
|---|---|---|---|---|---|---|---|---|
| | | Reagent Source, | Ease of | Appearance | | | | Loss of Alpha |
| | BF$_3$.Alcohol | Example | Mixing and | Upper Layer | | Lower Layer | | Olefin |
| Example | Reagent | No. | Settling | Sludge | Color | Viscosity | Color | IR, % |
| 12. | BF$_3$ Alone | — | No Settling Layer | Copious | Black | — | — | — |
| 13. | BF$_3$.Methanol | 1 | Good | No | Brown, Clear | Low | Black | 9 |
| 14. | BF$_3$.n-Butanol | 2 | Good | No | Brown, Clear | Low | Black | 19 |
| 15. | BF$_3$.n-Hexanol | 3 | No Settling Layer | No | Dk Brown | — | — | 63 |
| 16. | BF$_3$.n-Decanol | 4 | No Settling Layer | No | Dk Brown | — | — | 16 |
| 17. | BF$_3$.Ethylene Glycol | 5 | Hard to Mix, Slow Settling | No | Green/Brown | Viscous | Black | 0 |
| 18. | BF$_3$.Glycerine | 6 | Could Not Mix Well | — | — | — | — | — |
| 19. | BF$_3$ Methanol Ethylene Glycol | 9 | Rapid Phase Separation | No | Green/Brown | Low | Black | 11 |
| 20. | BF$_3$ Methanol Glycerine | 11 | Rapid Phase Separation | No | Green/Brown | Low | Black | 10 |

Examples 21 to 23

Three experiments were conducted as in Example 19 using the BF$_3$.Methanol.Ethylene Glycol treating agent to purify other predominantly straight chain olefins. In each case, before and after treatment, the sulfuric acid test was applied, that is, shaking 5 ml with 1 drop of concentrated sulfuric acid for 30 seconds, and a definite improvement in quality was obtained. The results are shown in Table IV.

TABLE IV

| | | Sulfuric Acid Test | |
|---|---|---|---|
| Example | Olefin Treated | Before Treat | After Treat |
| 21. | C$_{6-7}$ Cracked wax Alpha Olefin | Very Dark Much Sludge | Dark, Clear, No Sludge |
| 22. | C$_{15-18}$ Cracked Wax Alpha Olefin | Brown, Opaque | Dark Amber, Clear |
| 23. | Oligomer from C$_{10}$ Cracked Wax Olefin (89% Trimer, Tetramer and Pentamer) | Black, Opaque | Red-Brown, Opaque |

Example 24

An experiment was conducted as in Example 19 but applying three consecutive extractions with 2.5 g of BF$_3$ solution to 100 ml of olefin. Each step consisted of mixing, settling and withdrawing the black lower layer. The treated upper layer was washed with base, washed with water, and dried. In the sulfuric acid test, it gave a clear light brown color and no sludge. Only a slight amount of isomerization and polymerization of the 1-decene was observed by IR and gas chromatography techniques.

Example 25

Three oligomerizations of 1-decene were performed using techniques described in the literature. A BF$_3$.Butanol catalyst was added over one hour while bubbling BF$_3$ gas through the well-stirred olefin kept at about 75° F. After continuing the reaction for another ½ to 1½ hours, the product was washed with base, washed with water, and dried.

This procedure was run very satisfactorily on an ethylene-derived 1-decene using 2 wt % BF$_3$.Butanol catalyst. With a cracked wax 1-decene, the reaction did not go as well. More catalyst (3.6%) was needed, dark solids formed in the reaction mix and difficult emulsions were obtained on work-up. With the treated cracked wax 1-decene from Example 24, 2% catalyst worked well, no solids formed in the reaction mix, and no emulsion formed during work-up.

What is claimed is:

1. A process for purifying predominantly straight chain liquid olefins having from 5 to 50 carbon atoms which comprises contacting the olefins with a liquid solution of boron trifluoride in an alcohol or mixture of alcohols selected from the group consisting of mono and poly hydroxylic aliphatic compounds having from one to five carbon atoms, intimately admixing the liquid olefins and liquid solution of boron trifluoride, separating into two liquid layers, and recovering the olefin layer, under reaction conditions sufficient to minimize the olefinic reactions normally catalyzed by boron trifluoride while recovering an olefin product essentially free of color-forming impurities and impurities which retard or suppress further reaction of the olefins.

2. The process according to claim 1, wherein the olefin is an alpha olefin having from 5 to 25 carbon atoms obtained by the cracking of petroleum waxes.

3. The process according to claim 1, wherein a mixture of alcohols is employed.

4. The process according to claim 3, wherein the mixture of alcohols is a mixture of a mono-ol and a poly-ol.

5. The process according to claim 4, wherein the mixture of alcohols is a mixture of methanol and ethylene glycol.

6. The process according to claim 1, wherein the solution of boron trifluoride in an alcohol or mixture of alcohols contains from about 0.1 mole of boron trifluoride per mole of hydroxyl group up to saturation of the hydroxyl groups with boron trifluoride.

7. The process according to claim 1, wherein the contacting takes place at a temperature of from about $-20°$ C. to about 80° C.

8. The process according to claim 1, wherein the contacting takes place for a period of time from about 15 seconds to five minutes.

9. The process according to claim 1, wherein the ratio of boron trifluoride-alcohol to olefin is between about 0.01:100 and 10:100, on a weight basis.

* * * * *